United States Patent [19]

Mosnier et al.

[11] Patent Number: 4,652,583

[45] Date of Patent: Mar. 24, 1987

[54] USE OF NAFTIDROFURYL TO REGENERATE NERVE FIBERS

[75] Inventors: Michel Mosnier, Charenton-le-Pont; Marcel Grand, Lyons, both of France

[73] Assignee: Lipha, Lyonnaise Industrielle Pharmaceutique, Lyons, France

[21] Appl. No.: 852,940

[22] Filed: Apr. 17, 1986

[30] Foreign Application Priority Data

Apr. 23, 1985 [FR] France .................................. 85 06132

[51] Int. Cl.$^4$ ............................................ A61U 31/34
[52] U.S. Cl. .................................................... 514/461
[58] Field of Search .......................................... 514/461

[56] References Cited

U.S. PATENT DOCUMENTS

| 3,257,420 | 6/1966 | Szarvasi et al. | 514/471 |
| 3,334,096 | 8/1967 | Szarvasi et al. | 514/471 |
| 3,445,574 | 5/1969 | Szarvasi et al. | 514/471 |
| 4,439,442 | 3/1984 | Chick et al. | 549/496 |

FOREIGN PATENT DOCUMENTS 3843M  1/1966  France .

OTHER PUBLICATIONS

C. R. Acad. Sc. Paris, France, t. 262, pp. 719–721, (Feb. 7, 1966), Series D Pharmacodynamics and English language translation thereof.

Primary Examiner—Stanley J. Friedman
Attorney, Agent, or Firm—Browdy and Neimark

[57] ABSTRACT

Naftidrofuryl can be used to prepare a pharmaceutical which promotes the regeneration of nerve fibers. A neurologically active quantity of N,N-2-diethylaminoethyl-tetrahydro-alpha-(1-naphthylmethyl)-2-furan-propanoate or an addition salt thereof is incorporated in an excipient or an inert, nontoxic, pharmaceutically acceptable vehicle.

13 Claims, No Drawings

USE OF NAFTIDROFURYL TO REGENERATE NERVE FIBERS

FIELD OF THE INVENTION

The present invention relates to the use of N,N-2-diethylaminoethyl-tetrahydro-alpha-(1-naphthylmethyl)-2-furanpropanoate and its addition salts for the preparation of a medicine for a new therapeutic application for treatment of neuropathies of various origins.

BACKGROUND OF THE INVENTION

It is known that nerve fiber is endowed with a great ability for regeneration provided that the cellular bodies of the neurons have not degenerated or been destroyed. This physiological phenomenon of axonal regeneration aims at making possible a resumption of functional activity. However, this regeneration is relatively slow, and, considering the length of the segment to be regenerated, the functional recovery can take one to several years depending on the nature of the injured nerve.

Among disorders of the nervous system, neuropathies having axonal degeneration, by their frequency, represent a major cause of suffering and disability in the world, which explains why many attempts have been made to speed up the regrowth of the nerves. Various agents have been used for this purpose with varied successes, but most often have turned out to be toxic in the doses that make it possible to obtain a positive action on nerve growth.

U.S. Pat. No. 1,289,597, in particular addition 83.555 and French Pat. No. 1,363,948, show the physical constants and methods of preparing N,N-2-diethylaminoethyl-tetrahydro-alpha-(1-naphthylmethyl)-2-furanpropanoate represented by the formula

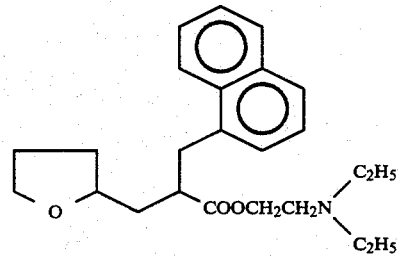

Further, special medicine Pat. No. 3.843M, discloses that N,N-2-diethylaminoethyl-tetrahydro-alpha-(1-naphthylmethyl)-2-furanpropanoate, commonly designated "Naftidrofuryl," and its salts of organic or inorganic acids are endowed with antispasmodic and vasodilative properties. Of these compounds, "Naftidrofuryl" oxalate constitutes the active ingredient of medicines used in human medicine for their vasodilative action.

Naftidrofuryl has been the subject of a large number of scientific works in various countries for about twenty years; it is also known as an activator of the metabolism of glucose in the cerebral cell and as a cerebral vasodilator. Recent studies (S. Kobayashi et al. *Arzneimittel Forschung* 34, 1984, pp. (1580–1583) have shown its faborable effect on cerebral circulation after acute cerebral infarctus. Naftidrofuryl improves the regional cerebral flow in the ischemic cerebral zones. The treatment of venous ulcers with Naftidrofuryl was studied at the Regional Hospital Center of Reims, *J. Mal. Vasc.* (France), 1984, 9 (2) pp. 133–6, and the effectiveness of Naftidrofurylin on the occlusion of the arteries was checked by U. Maass et al, *Medizinische Hochschule Hanover, Dtsch. Med. Wochenschr* (F.R.G.) May 11, 1984, 109, pp. 745–50, and by Trubestein G. et al, *Angiology* (U.S.) Nov. 1984, 35, pp. 701–8.

SUMMARY OF THE INVENTION

It is an object of the present invention to provide a method of enhancing the growth of nerve fibers.

It has been discovered in an entirely surprising and unexpected way that and its addition salts exert an effect completely separate from the actions already known, on the growth of nerve cells and thus constitute a highly significant nerve growth factor.

This effect has no relation to the already established effects of Naftidrofuryl. It has been found that Naftidrofuryl and its acid addition salts has the ability to regenerate nerve fibers, which makes their use particularly advantageous as active ingredients of medicines that find their application in the treatment of neuropathies of varied origins, such as for example, post-traumatic neuropathies, diabetic neuropathies, certain toxic neuropathies such as ethylic polyneuritises or the neuropathies of bacterial or viral origin and degenerative neuropathies.

Naftidrofuryl and its addition salts are also used to reestablish and the perception of pain at the skin level after surgical intervention.

Both the racemic compound and the diastereoisomers A and B or the optical antipodes d and l of the diastereoisomers A and B are included in the denomination Naftidrofuryl. The denomination Naftidrofuryl also includes the diastereoisomers A and B in a mixture of any proportions.

The addition salts of Naftidrofuryl with pharmaceutically acceptable acids, include the salts made with inorganic acids: hydrochloric, hydrobromic, hydriodic, nitric, sulfuric, phosphoric, and with organic acids: formic, benzoic, fumaric, succinic, tartric, citric, oxalic, glyoxylic, aspartic, alkanesulfonic and arylsulfonic. The polyacid salts of Naftidrofuryl such as oxalate, fumarate and citrate exhibit a particular advantage as an active ingredient in the production of medicines that regenerate nerve fibers.

The medicines produced for the new therapeutic application contain a neurologically effective quantity of Naftidrofuryl or of one of its addition salts in a mixture or in association with an inert, nontoxic, pharmaceutically acceptable excipient or vehicle.

The medicines can be produced in various pharmaceutical forms, including those which are suited to oral administration such as uncoated or coated tablets, pills, microgranules, tablets having several cores, capsules, powders or granules.

Forms which are suited for parenteral administration comprise injectable suspensions or aqueous solutions distributed in ampules, in multi-drop bottles or in syringes ready for injection.

Suitable forms for rectal administration include suppositories or rectal capsules.

The toxicity of Naftidrofuryl and of its addition salts is slight, thus the lethal dose LD 50 of Naftidrofuryl oxalate on mice per os is 365 mg/kg and intraperitoneally 225 mg/kg and on rats p.o. 1,732 mg/kg and i.p. 136 mg/kg.

The daily dose of active ingredient orally is between 300 mg and 1.5 g, and by vein optionally as perfusion, between 400 and 1,200 mg, preferably 800 to 1200 mg.

The medicines according to the invention contain from 0.100 to 1 g of Naftidrofuryl or of one of its addition salts and preferably 200 to 400 mg per unit dose.

These medicines containing Naftidrofuryl or one of its addition salts as active ingredient can further include another active ingredient with synergic action, particularly any ingredient that improves the resorption or the diffusion of the active ingredient in the organism.

The following nonlimiting examples demonstrate the new therapeutic application of Naftidrofuryl.

DETAILED DESCRIPTION OF THE INVENTION

EXAMPLE I

| Capsule containing 100 mg of Naftidrofuryl oxalate (LS 121) | |
| --- | --- |
| LS 121 | 100 mg |
| Talc | 37 mg |
| Magnesium stearate | 3 mg |
| | 140 mg |
| capsule size 4:1 capsule | |

EXAMPLE II

| Tablet containing 300 mg of Naftidrofuryl oxalate. | |
| --- | --- |
| LS 121 | 300 mg |
| Copolymers of dimethylaminoethyl methacrylate and neutral esters of methacrylic acid | 100 mg |
| Tricalcium phosphate | 38 mg |
| Talc | 10 mg |
| Magnesium stearate | 2 mg |
| | 450 mg |

EXAMPLE III

| Injectable form having 200 mg of active ingredient | | |
| --- | --- | --- |
| LS 121 | | 200 mg |
| Sorbitol | | 400 mg |
| water p.p.i. | q.s.p. | 10 ml |

EXAMPLE IV

| Microgranules having 200 mg of active ingredient | |
| --- | --- |
| LS 121 | 200 mg |
| Corn starch | 15 mg |
| Gum lac | 19 mg |
| Polyvidone excipient | 9.5 mg |
| Polyoxyethylene glycol 4000 | 10 mg |
| Saccharose | 40 mg |
| Talc | 19 mg |
| capsule size 1:1 capsule | 312.5 mg |

EXAMPLE V

Pharmacological study

The ability to promote nerve growth of the polyacid addition polyacid salts of Naftidrofuryl, such as oxalate, fumarate and citrate, has been demonstrated by various tests, in particular that of the spinal ganglia of the rat, described below.

The tests were performed on lumbar and dorsal spinal ganglia taken on the twentieth day from Wister rat embryos "in utero."

These ganglia were grown in a Leighton tube on slides covered with a film of reconstituted rat tail collagen under normal atmosphere in Dulbecco medium modified by N. Iscove and F. Melchers [J. Exp. Med., 147, 923 (1978)] to which 8% fetal calf serum and glucose were added in a ratio of 6 g per liter.

The notation and measurement were made of the length of the nerve extensions and of the zone of cell growth put out in 48 hours of culture under the action of the studied compound used in three molar dilutions $10^{-6}$, $10^{-7}$ and $10^{-8}$, in comparison with control cultures.

The observations were made under the microscope after impregnation, by silver, of the cultures "in toto" according to the Bodian method [Anat. Record. 69, 153–162 (1937)], mounted on coded strips.

Three experiments each comprising between 15 and 25 ganglia in the experimental and control groups were made.

The results for the weakest dilutions of $10^{-7}$ and $10^{-8}$M have been gathered in Tables I and II; it appears that this compound is capable of increasing in a very significant statistical fashion in relation to the controls, the number of extensions put out in 48 hours, the diameter of the growth zone and the length of the nerve extensions.

It should be emphasized that the optimal active concentration of $10^{-7}$ mole per liter of Naftidrofuryl oxalate is remarkably slight and that it is less than the useful therapeutic concentration of this compound as a vasodilator.

Virtually similar results were obtained with the addition salts of Naftidrofuryl, particularly with the polyacid salts.

TABLE I

| | Raw Data | | | | | | | | |
| --- | --- | --- | --- | --- | --- | --- | --- | --- | --- |
| | Number of Ganglia | Averages | Standard Deviations | Number of Ganglia | Averages | Standard Deviations | Number of Ganglia | Averages | Standard Deviations |
| $T_1$ | 25 | 191.7 | 62.86 | 25 | 39.40 | 7.30 | 25 | 38.37 | 6.92 |
| $10^{-6}$ | 24 | 192.2 | 72.66 | 24 | 34.50 | 7.34 | 24 | 36.02 | 7.86 |
| $10^{-7}$ | 25 | 248.28 | 93.30 | 25 | 42.80 | 8.50 | 25 | 42.35 | 8.65 |
| $T_2$ | 20 | 109.90 | 68.35 | 20 | 24.37 | 5.45 | 20 | 20.95 | 4.64 |
| $10^{-7}$ | 18 | 142.90 | 58.56 | 18 | 31.56 | 7.27 | 17 | 28.80 | 7.34 |
| $10^{-8}$ | 16 | 133.93 | 54.38 | 16 | 29.40 | 6.30 | 16 | 26.35 | 6.28 |
| $T_3$ | 15 | 157.60 | 86.65 | 15 | 30.02 | 7.54 | 15 | 28.24 | 10.59 |
| $10^{-7}$ | 17 | 193.35 | 11.30 | 17 | 35.90 | 10.60 | 17 | 34.70 | 11.00 |
| $10^{-8}$ | 18 | 195.05 | 79.30 | 18 | 39.00 | 9.50 | 18 | 38.23 | 10.40 |
| | Number of extensions | | | Length of Cellular Growth Zone | | | Length of extensions | | |

TABLE II

| | | Corrected Data (Comparison of the Averages and Student Test) | | | | | | | | | | |
|---|---|---|---|---|---|---|---|---|---|---|---|---|
| | Number of Ganglia | Number of Extensions | | | | Length of the Cellular Growth Zone | | | | Length of the Extensions | | | |
| | | Averages | Standard Deviations | t | p | Averages | Standard Deviations | t | p | Averages | Standard Deviations | t | p |
| Controls | 60 | 155.9 | 78.45 | | | 32.05 | 9.42 | | | 30.04 | 10.55 | | |
| $10^{-7}$ | 60 | 201.1 | 88.02 | 2.84 | 0.0054 | 37.76 | 9.43 | 3.32 | 0.0012 | 36.55 | 9.97 | 3.46 | 0.0004 |
| $10^{-8}$ | 34 | 219.9 | 110.12 | 3.27 | 0.0016 | 40.25 | 9.28 | 4.07 | <0.0001 | 39.30 | 10.12 | 4.15 | <0.0001 |

It can thus be seen that the objects set forth above, among those made apparent from the preceding description, are efficiently attained. Since certain changes may be made in carrying out the invention without departing from the scope of the claims, it is intended that all matter contained in the above description or shown in the accompanying drawings shall be interpreted as illustrative and not limiting.

What is claimed is:

1. A method for promoting the regeneration of nerve fibers comprising administering to a living organism in need of the regeneration of a nerve fiber an amount of N,N-2-diethylaminoethyl-tetrahydroalpha-(1-naphthylmethyl)-2-furanpropanoate effective to regenerate said nerve fiber.

2. The method of claim 1 wherein the N-N-2-diethylaminoethyl-tetrahydro-alpha-(1-naphthylmethyl)-2-furanpropanoate is incorporated into an inert, nontoxic, pharmaceutically acceptable vehicle to form a pharmaceutically acceptable composition.

3. The method of claim 2 wherein the N-N-diethylaminoethyl-tetrahydro-alpha-(1-naphthylmethyl)-2-furanpropanoate is in the form of an addition salt with a pharmaceutically acceptable acid.

4. The method of claim 3 wherein the pharmaceutically acceptable acid is selected from the group consisting of hydrochloric, hydrobromic, hydriodic, nitric, sulfuric, phosphoric, formic, benzoic, fumaric, succinic, tartric, citric, oxalic, glyoxylic, aspartic, alkanesulfonic, and arylsulfonic acids.

5. The method of claim 1 wherein the N-N-2-diethylaminoethyl-tetrahydro-alpha-(1-naphthylmethyl)-2-furanpropanoate is in the form of a salt of a polyacid selected from the group consisting of oxalate, fumarate, and citrate.

6. The method of claim 2 wherein the amount of N,N-2-diethylaminoethyl-tetrahydro-alpha-(1-naphthylmethyl)-2-furanpropanoate is from about 0.100 g to about 1 g per unit dose.

7. The method of claim 6 wherein the amount of N-N-2-diethylaminoethyl-tetrahydro-alpha-(1-naphthylmethyl)-2-furanpropanoate is from about 200 to 400 mg. per unit dose.

8. The method of claim 2 wherein the vehicle is selected from coated tablets, uncoated tablets, pills, microgranules, tablets having more than one core, capsules, powders, granules, aqueous solutions, injectable suspensions rectal suppositories, and rectal capsules.

9. The method of claim 2 wherein the pharmaceutically acceptable composition is administered orally.

10. The method of claim 2 wherein the pharmaceutically acceptable composition is administered parenterally.

11. The method of claim 2 wherein the pharmaceutically acceptable composition is administered rectally.

12. The method of claim 9 wherein the daily dosage of N,N-2-diethylaminoethyl-tetrahydro-alpha-(1-naphthylmethyl)-2-furanpropanoate is from about 300 mg. to about 1.5 mg.

13. The method of claim 10 wherein the daily dosage of N,N-2-diethylaminoethyl-tetrahydro-alpha-(1-naphthylmethyl)-2-furanpropanoate is from about 400 to about 1200 mg.

* * * * *